US008588504B2

(12) United States Patent
Yano et al.

(10) Patent No.: US 8,588,504 B2
(45) Date of Patent: Nov. 19, 2013

(54) TECHNIQUE FOR DETERMINING THE STATE OF A CELL AGGREGATION IMAGE PROCESSING PROGRAM AND IMAGE PROCESSING DEVICE USING THE TECHNIQUE, AND METHOD FOR PRODUCING A CELL AGGREGATION

(75) Inventors: Kazuhiro Yano, Yokohama (JP); Masafumi Mimura, Ageo (JP); Kei Ito, Okegawa (JP); Hideki Sasaki, Yokohama (JP)

(73) Assignee: Nikon Corporation, Tokyo (JP)

( * ) Notice: Subject to any disclaimer, the term of this patent is extended or adjusted under 35 U.S.C. 154(b) by 128 days.

(21) Appl. No.: 13/315,794

(22) Filed: Dec. 9, 2011

(65) Prior Publication Data

US 2012/0142095 A1 Jun. 7, 2012

Related U.S. Application Data

(63) Continuation of application No. PCT/JP2010/003822, filed on Jun. 8, 2010.

(30) Foreign Application Priority Data

Jun. 12, 2009 (JP) ................................. 2009-141371

(51) Int. Cl.
*G06K 9/00* (2006.01)
*C12N 5/00* (2006.01)

(52) U.S. Cl.
USPC ............................ 382/133; 382/172; 435/422

(58) Field of Classification Search
USPC ......... 382/100, 103, 106–107, 128–133, 162, 382/168, 172, 173, 181, 190, 194, 199, 203, 382/219, 232, 254, 274, 276, 286, 291, 305, 382/312; 435/283.1, 422; 530/388.22
See application file for complete search history.

(56) References Cited

U.S. PATENT DOCUMENTS 5,487,112 A 1/1996 Zygourakis et al.
8,053,238 B2 * 11/2011 Jin et al. ........................ 435/422
(Continued)

FOREIGN PATENT DOCUMENTS

EP 1 992 685 A1 11/2008
JP 2003-116593 4/2003
(Continued)

OTHER PUBLICATIONS

International Search Report for corresponding International Application PCT/JP2010/003822; mailed Sep. 7, 2010.
(Continued)

*Primary Examiner* — Seyed Azarian

(57) ABSTRACT

An image processing program (GP) attains (S10) time lapse images, extracts (S20) a cell aggregation from each of the obtained images, and calculates (S50), for the entire region of the cell aggregation, the spatial distribution in pixel values and temporal change in pixel values of a small region in the extracted cell aggregation. The program determines (S70) the state of change of the cell aggregation toward becoming multi-layered, on the basis of the calculated spatial distribution and time lapse change of pixel values, and outputs (S80) the results of the determination. The image processing program (GP) is configured so as to determine and output, from time lapse images, the state of change of the cell aggregation toward becoming multi-layered.

20 Claims, 8 Drawing Sheets

(56) References Cited

U.S. PATENT DOCUMENTS

| | | | |
|---|---|---|---|
| 8,265,357 B2 * | 9/2012 | Ramsing et al. | 382/128 |
| 8,329,471 B2 * | 12/2012 | Jin et al. | 435/422 |
| 8,344,113 B2 * | 1/2013 | Bamdad | 530/388.22 |
| 8,361,781 B2 * | 1/2013 | Morgan et al. | 435/283.1 |
| 2008/0247628 A1 | 10/2008 | Ramsing et al. | |

FOREIGN PATENT DOCUMENTS

| | | |
|---|---|---|
| JP | 2004-229619 | 8/2004 |
| JP | 2005-27623 | 2/2005 |
| JP | 2005-027623 | 2/2005 |
| JP | 2009-89629 | 4/2009 |
| JP | 2009-89630 | 4/2009 |
| JP | 2009-152827 | 7/2009 |
| WO | 2007/114351 | 10/2007 |
| WO | 2009/081832 | 7/2009 |

OTHER PUBLICATIONS

Nathalie Meyer et al. "A fluorescent reporter gene as a marker for ventricular specification in ES-derived cardiac cells" FEBS Lett. 2000, vol. 478, No. 1-2, pp. 151-158.

Shizuko Ichinose et al. "Hito Kan'yo Kansaibo o Mochiita Nankotsu Soshiki no Saisei", The Cell, 2007, vol. 39, No. 9, pp. 399-403.

International Search Report for related International Application PCT/JP2010/004597 mailed Sep. 14, 2010.

U.S. Appl. No. 13/359,074, filed Jan. 26, 2012, Masafumi Minura, et al., Nikon Corporation.

C. Urani et al: "Image Analysis and Automatic Classification of Transformed Foci", Journal of Microscopy, vol. 234, No. 3, May 18, 2009, pp. 269-279.

Extended European Search report issued Sep. 25, 2013 in European Patent Application No. 10785952.2-1906/2441827.

* cited by examiner

IMAGE AFTER SEGMENTATION
AND LABELING

TIME LAPSE
CELL AGGREGATION IMAGES (LABEL N)

EXTRACTED MULTI-LAYERING
SITE (SHADED PART)

TECHNIQUE FOR DETERMINING THE STATE OF A CELL AGGREGATION IMAGE PROCESSING PROGRAM AND IMAGE PROCESSING DEVICE USING THE TECHNIQUE, AND METHOD FOR PRODUCING A CELL AGGREGATION

This is a continuation of PCT International Application No. PCT/JP2010/003822, filed on Jun. 8, 2010, which is hereby incorporated by reference. This application also claims the benefit of Japanese Patent Application No. 2009-141371, filed in Japan on Jun. 12, 2009, which is hereby incorporated by reference.

TECHNICAL FIELD

The present invention relates to a state analysis technique for determining the state of change of a cell aggregation toward becoming multi-layered, from time-lapse images obtained during cell observation.

TECHNICAL BACKGROUND

A cell culture microscopy can be cited as an example of a device for observing a cell while the cell is being cultured. A cell culture microscopy is provided with a cell culture device for forming an environment suitable for culturing a cell, and a microscope observation system for microscopic observation of a cell in a cell culture container. The cell culture microscopy is configured so that changes, divisions, and other cell activities can be observed while the living cell is cultured (see Patent Document 1, for example). During the process of culturing a live cell, a cell aggregation is formed by the progression of cell division. During the initial stages of cell division, the divided cells spread out in the horizontal direction throughout the cell culture medium in a single-layered state, but as the activity of cell division intensifies and the cell aggregation matures, the cells also spread out in the up-down direction so as to form bubbles, and the "multi-layering" progresses.

In a conventional cell observation technique using a cell culture microscopy, the state of change of a cell aggregation toward becoming multi-layered is judged by a visual judgment, in which a determination is made by visual observation of a microscope observation image, and/or by a reagent judgment, in which a reagent is administered and a determination is made from the state of coloration or other parameter.

PRIOR ARTS LIST

Patent Document

Patent Document 1: Japanese Laid-open Patent Publication No. 2004-229619(A)

SUMMARY OF THE INVENTION

Problems to be Solved by the Invention

However, in order to extract a cell aggregation and determine, from a plurality of time lapse images, the state in which the cell aggregation has become multi-layered, the technique for visual judgment that has conventionally been employed requires that an expert having a certain amount of experience make the determination over a period of time. In particular, in a case in which the observation image at each instance includes a plurality of cell aggregations, determining the state(s) of change toward becoming multi-layered while still identifying individual cell aggregations is a very complex task. The visual judgment is also problematic in that it is difficult to quantitatively ascertain the position and/or size of a site in a cell aggregation that has become multi-layered (the ratio of the surface area and/or cell aggregations, or another parameter). The technique for a reagent judgment has been further problematic in that administering the reagent has a major chemical and physical effect on the cells, and in that there are major constraints in using cultured cells.

The present invention was developed in view of such problems, it being an object of the present invention to provide means by which the state of change of a cell aggregation toward becoming multi-layered can be determined from time lapse images taken by an imaging device without there being damage to the cells due to the administration of a reagent.

Means to Solve the Problems

According to a first aspect illustrating an example of the present invention, there is provided a technique for determining the state of a cell aggregation comprising the steps of obtaining time lapse images of a cell aggregation taken by an imaging device; calculating a spatial distribution of pixel values and a temporal change of pixel values of a small region in the cell aggregation in the obtained images; and determining a state of change of the cell aggregation toward becoming multi-layered on the basis of the calculated spatial distribution and time lapse change of the pixel values.

According to a second aspect illustrating an example of the present invention, there is provided an image processing program that can be read out by a computer, the image processing program being adapted for causing the computer to function as an image processing device for obtaining an image taken by an imaging device and performing image processing so as that the state of change of a cell aggregation toward becoming multi-layered is determined from time lapse images of the cell aggregation and outputted, comprising the steps of obtaining time lapse images of a cell aggregation taken by an imaging device; calculating the spatial distribution in pixel values and temporal change in pixel values of a small region in the cell aggregation in the obtained images; determining the state of change of the cell aggregation toward becoming multi-layered on the basis of the calculated spatial distribution and time lapse change of the pixel values; and outputting the determination results.

According to a third aspect illustrating an example of the present invention, there is configured an image processing device provided with an image analysis unit for obtaining time lapse images of a cell aggregation taken by an imaging device and analyzing the images, and an output unit for outputting the analysis results from the image analysis unit. The image processing device is configured such that the image analysis unit calculates the spatial distribution of pixel values and the temporal change of pixel values of a small region in a cell aggregation within the obtained images, and determines the state of change of the cell aggregation toward becoming multi-layered, on the basis of the calculated spatial distribution and time lapse changes of the pixel values; and the output unit outputs the state of change of the cell aggregation toward becoming multi-layered as determined by the image analysis unit.

In the present invention described above, the determination of the state of change toward becoming multi-layered is preferably such that a cell aggregation is determined to have become multi-layered in a case in which the spatial change in pixel values within the small region is at or above a threshold value and also the change in temporal pixel values is at or above a threshold value. In such a case, the spatial change in pixel values is preferably the variance of pixel values or derivative sum of pixel values in the small region, and the temporal change in pixel values is preferably the variance or derivative of the pixel values of corresponding small regions in the time lapse images.

The image processing program or image processing device of the present invention, in a preferred configuration, outputs position information for a cell aggregation at a site where multi-layering is decided to have occurred, and, in a preferred configuration, outputs information on the size of the cell aggregation that accounts for the site where multi-layering is decided to have occurred (the surface area, the volume, the ratio thereof, or the like). In a preferred configuration, in a case in which individual images in a time lapse include a plurality of cell aggregations, the state of a change toward becoming multi-layered is determined for each cell aggregation; a distinction is made between cell aggregations having multi-layered sites and cell aggregations not having multi-layered sites, and the determination results that have been distinguished are outputted.

According to a fourth aspect illustrating an example of the present invention, there is provided a method for producing a cell aggregation, comprising a cell culture step for culturing cells, and a determination step for observing, using the image processing device according to any of Claims 12 to 18, the cells cultured in the cell culture step, and determining the state of change of a cell aggregation toward becoming multi-layered in the cells, which vary by cell culture.

According to a fifth aspect illustrating an example of the present invention, there is provided a method for producing a cell aggregation, comprising a cell culture step for culturing cells; an obtainment step for taking an image, by an imaging device, of the cells cultured in the cell culture step and obtaining time lapse images of a cell aggregation in the cells, which vary by cell culture; a calculation step for calculating the spatial distribution of pixel values and the temporal change in pixel values of a small region in a cell aggregation that is in the time lapse images obtained in the obtainment step; and a determination step for determining the state of change of a cell aggregation toward becoming multi-layered on the basis of the spatial distribution and time lapse change of the pixel values calculated in the calculation step.

Advantageous Effects of the Invention

In the technique for determining the state of a cell aggregation, the image processing program, and the image processing device of the present invention, the state of change of a cell aggregation toward becoming multi-layered is determined from the spatial luminance distribution and the temporal luminance change of a small region of a cell aggregation. Therefore, according to the present invention, there can be provided means by which the state of change of a cell aggregation toward becoming multi-layered can be determined from time lapse images taken by an imaging device without the cells being damaged due to the administration of a reagent.

DESCRIPTION OF THE EMBODIMENTS

Figure 2:
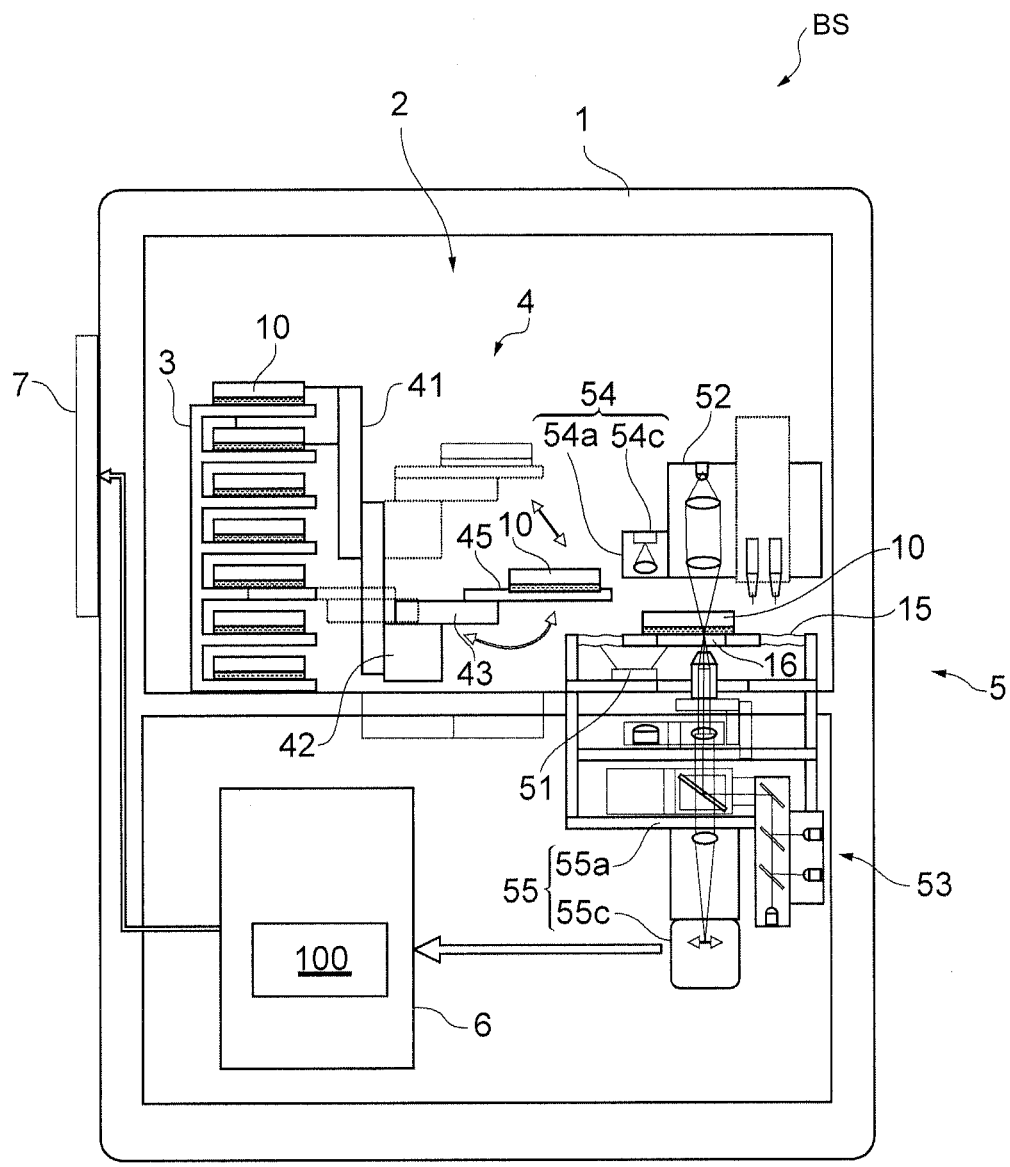
FIG. 2 is a diagram providing a rough structural view of a cell culture observation system illustrated as an example of the application of the present invention.
Figure 3:
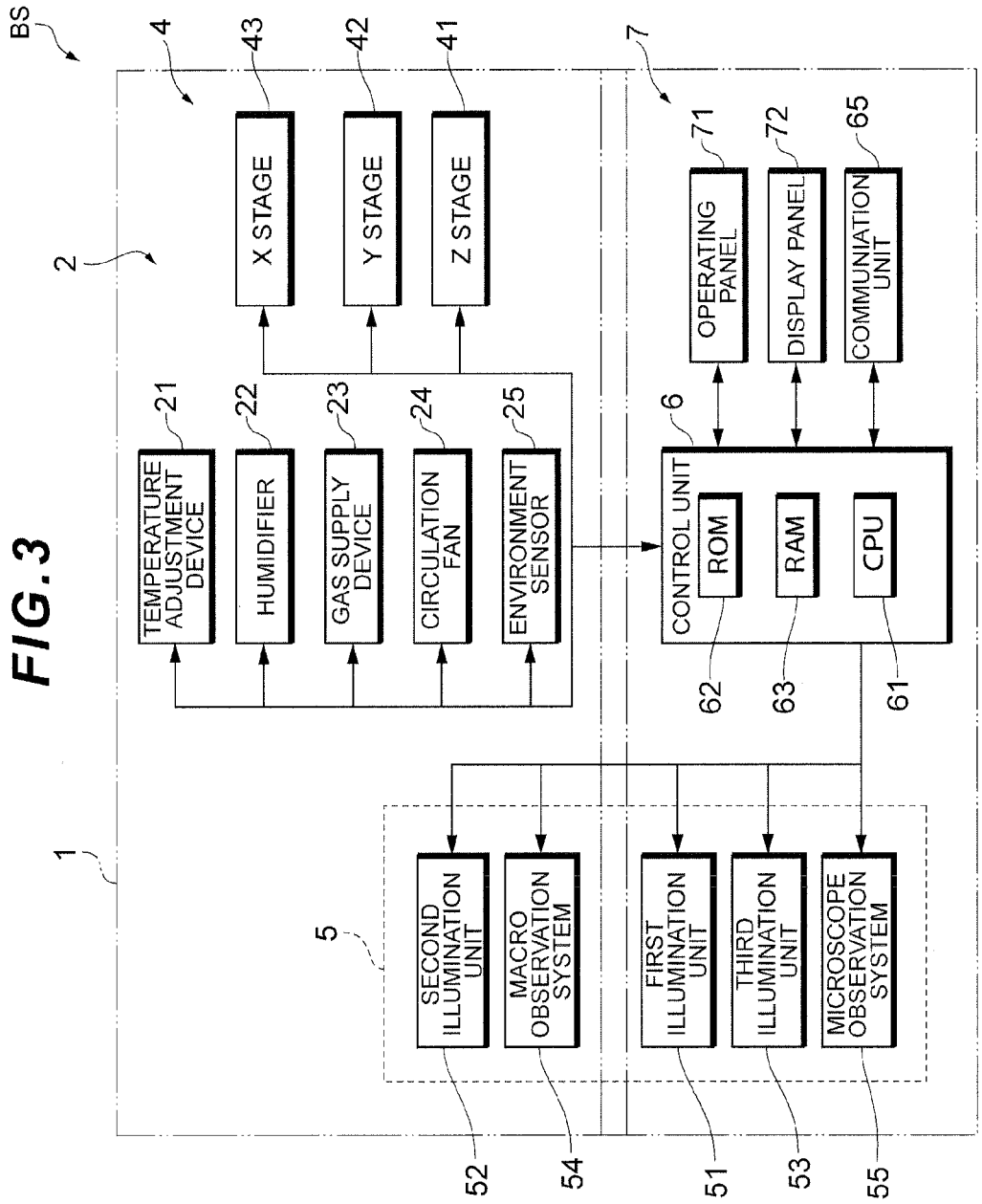
FIG. 3 is a block diagram of the aforementioned cell culture observation system.

Embodiments of the present invention will be described hereinafter with reference to the accompanying drawings. As an example of a system in which the image processing device of the present invention has been applied, FIGS. 2 and 3 illustrate a rough structural view and a block diagram of a cell culture observation system. First, a description of the overall configuration of a cell culture observation system BS will be summarized.

The cell culture observation system BS is primarily constituted of a cell culture chamber 2 provided to a top part of a chassis 1; a stocker 3 for accommodating and retaining a plurality of cell culture containers 10; an observation unit 5 for observing samples in the cell culture containers 10; a conveyance unit 4 for conveying the cell culture containers 10; a control unit 6 for controlling the operation of the system; an operating board 7 provided with an image display device; and other components.

The cell culture chamber 2 is a compartment for forming a cell culture environment, and the cell culture chamber 2 is additionally provided with such components as a temperature adjustment device 21; a humidifier 22; a gas supply device 23 for supplying $CO_2$ gas, $N_2$ gas, or other gas; a circulation fan 24; and an environment sensor 25 for detecting the temperature, humidity, and other features of the cell culture chamber 2. The stocker 3 is formed in a shelf shape partitioned in the front-rear and up-down directions, a specific number being set for each shelf. The cell culture container 10 is appropriately selected according to the type or purpose of the cell to be cultured; cell samples are injected together with a liquid cell culture medium and retained in, for example, dish-type cell culture containers. A code number is assigned to each of the cell culture containers 10, which are associated with a designated number and accommodated in the stocker 3. The conveyance unit 4 comprises such components as a Z stage 41 capable of moving up and down, a Y stage 42 capable of moving forward and backward, and an X stage 43 capable of moving left and right, these stages being provided within the cell culture chamber 2. A support arm 45 for lifting and supporting a cell culture container 10 is provided toward the distal end of the X stage 43.

The observation unit 5 is constituted of such components as a first illumination unit 51 for illuminating a sample from a lower side of a sample stage 15; a second illumination unit 52 for illuminating the sample along the optical axis of a microscope observation system 55 from above the sample stage 15; a third illumination unit 53 for illuminating the sample from below; a macro observation system 54 for macro observation of the sample; a microscope observation system 55 for micro observation of the sample; and an image processing device 100. A transparent window part 16 is provided to the sample stage 15, in the region thereof observed by the microscope observation system 55.

The macro observation system 54 is configured to have an observation optical system 54a and a CCD camera or other imaging device 54c for taking an image of a sample that is imaged by the observation optical system. An overall observation image (macro image) is obtained from above the cell culture container 10, which is backlit by the first illumination unit 51. The microscope observation system 55 is configured to have an observation optical system 55a comprising an objective lens, a middle zooming lens, a fluorescence filter, and other components; and a cooled CCD camera or other imaging device 55c for taking an image of the sample imaged by the observation optical system 55a. The objective lenses and middle zooming lenses are provided in pluralities, and are configured such that the desired magnification for observation can be set by altering the combination of lenses. The microscope observation system 55 obtains a transmittance image of a cell illuminated by the second illumination unit 52; a reflection image of a cell illuminated by the third illumination unit 53; a fluorescence image of a cell illuminated by the third illumination unit 53, and other microscope observation images (micro images) in which the cell inside the cell culture container 10 is microscopically observed.

Images are taken by the imaging device 54c of the macro observation system 54 and the imaging device 55c of the micro observation system 55, the image processing device 100 processing the signals inputted from these imaging devices; and generating an image of the overall observation image, the micro observation image, or the like. The image processing device 100 applies image analysis to the (image data of the) observation images, and generates a time lapse image, predicts a movement direction of a cell, analyzes the degree of activity of a cell, analyzes the motion state of the cell, analyzes the state of change of a cell aggregation toward becoming multi-layered, and performs other processing. The image processing device 100 will be described in detail hereinafter.

The control unit 6 has a CPU 61 for executing processes; a ROM 62 in which a control program, control data, or the like for the cell culture observation system BS are set and stored; and a RAM 63 for temporarily storing observation conditions, image data, and the like, which comprises a hard drive, DVD, or other auxiliary memory device; and other components; and controls operation of the cell culture observation system BS. Therefore, as illustrated in FIG. 3, the respective constituent instruments of the cell culture chamber 2, the conveyance unit 4, the observation unit 5, and the operating board 7 are connected to the control unit 6. Environment conditions of the cell culture chamber 2, an observation schedule, and observation classifications, observation positions, observation magnifications, and other information for the observation unit 5 are set and stored in the RAM 63, in accordance with the observation program. The RAM 63 is also provided with an image data memory region for recording image data taken by the observation unit 5. Index data, which include a code number of the cell culture container 10, an image-capture time, and other information are recorded in association with image data.

The operating board 7 is provided with an operating panel 71 to which a keyboard, switch, or other input/output instrument is provided; and with a display panel 72 for displaying an operating screen, an observation image, analysis results, or the like. On the operation panel 71, the observation program is set, the conditions are selected, and an operational instruction or the like is inputted. A communication unit 65 is configured to conform to a wired or wireless communication standard, permitting data to be sent from and received by a computer or the like that is externally connected to the communication unit 65.

In the cell culture observation system BS thus generally configured, the CPU 61 controls the operation of each of the components and automatically photographs the sample in the cell culture container 10, in accordance with the observation program that has been set in the operating board 7. When the observation program is started, the CPU 61 controls the operation of the temperature adjustment device 21, the humidifier 22, and the like, on the basis of the environment conditions stored in the RAM 63. The observation conditions stored in the RAM 63 are read in; the X, Y, and Z stages 43, 42, 41 are operated on the basis of the observation schedule; the cell culture container 10 that is to be observed is conveyed from the stocker 3 to the sample stage 15; and the observation by the observation unit 5 is initiated. In a case in which, for example, the observation that has been set in the observation program is micro observation of a cell, then the corresponding cell culture container 10 is positioned onto the optical axis of the microscope observation system 55, the light source of the second illumination unit 52 or the third illumination unit 53 is activated, and the imaging device 55c is made to take a microscopic observation image.

The cell culture observation system BS configured as described above has a function whereby the image processing device 100 obtains time lapse images taken by an image processing device (54c, 55c) and determines the state of change toward becoming multi-layered of a cell aggregation included in the image; and can be used appropriately to analyze, for example, iPS cells, ES cells, or the like. For time lapse images in which a cell aggregation is photographed, the image processing device 100 decides from the spatial and temporal features of the luminance distribution whether or not the cell aggregation has become multi-layered. Such technique makes use of the fact that the image at a site where multi-layering has occurred has the following two characteristics.

(A) In a cell aggregation, the luminance distribution of a portion in which multi-layering has progressed has a greater spatial change in luminance (disparity in pixel values) than the luminance distribution of a portion that has not become multi-layered. Presumably this is because a single-layer region in which the cells have not become multi-layered does not have quite as great a spatial change in luminance within a small region because the cell aggregation spreads out in the horizontal direction, whereas a multi-layered region has a larger spatial change in luminance within the small region, because the cells swell upward so as to form bubbles.

(B) The time scale of luminance changes created in a portion where multi-layering has progressed is shorter than that of the luminance changes in a portion that has not become multi-layered or than that of the luminance changes caused by the changes in the cell aggregation boundaries. As described above, this is presumably because a multi-layered region has greater fluctuations of the luminance of the small region in a shorter period of time, because the cells spread out so as to form bubbles.

Figure 5:
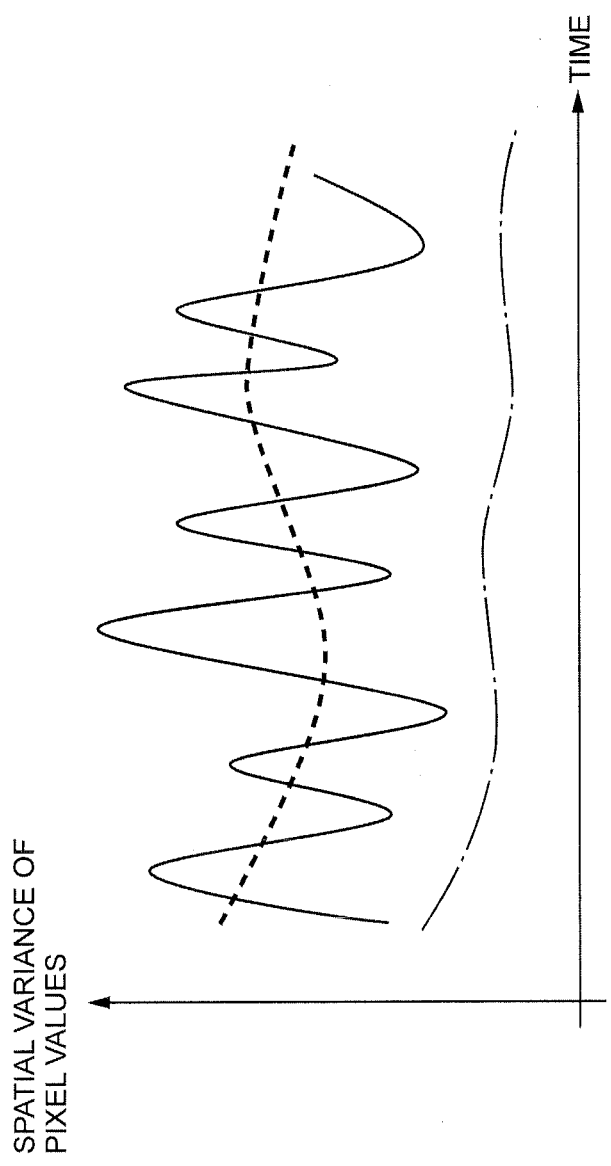
FIG. 5 is a graph illustrating the manner in which spatial distribution varies over the time lapse, where the vertical axis is the spatial distribution of pixel values in a small area, and the horizontal axis is time.

Specifically, FIG. 5 illustrates when a sufficiently small region, which is smaller than the size of the cell aggregation, is designated and the spatial change of the luminance of the small region and the temporal change thereof are plotted for time lapse images in which a cell aggregation that is being cultured is photographed. In FIG. 5, where the vertical axis is the spatial variance of pixel values of a small region (e.g., the variance of pixel values in a small region 20×20 pixels in size (the size of two to three cells)), and the horizontal axis is time, the state of change in the spatial variance of pixel values of a small region is schematically illustrated for a small region that has become multi-layered (the solid line) and another small region (the dotted or double-dotted line).

The solid line in FIG. 5 illustrates the properties of the small region at a site where multi-layering has occurred. In the small region at a site where multi-layering has occurred, the spatial change in pixel values (the luminance variance) is larger and varies so as to fluctuate more in comparatively shorter cycles, due to the cells proliferating so as to form bubbles.

The dotted line in FIG. 5 illustrates the properties of a small region that includes the boundary (contour part) of the cell aggregation. Because the luminance at the boundary of the cell aggregation varies greatly between the contour lines, the pixel values have a comparatively greater spatial change (luminance variance). However, even assuming that the cell aggregation grows or shrinks and the boundaries of the cell aggregation shift, the speed of the shift is reduced and the pixel values have a slower and smaller temporal change.

The single-dotted line in FIG. 5 illustrates the properties of a small region at a site that has not become multi-layered. In the small region at a site in a single-layered state, even though the cell aggregation has spread out, the pixel values have a small spatial change, and the pixel values have a small temporal change as well.

The present invention, focusing on the above-described characteristics of a multi-layered region when imaged, runs image processing on time lapse images of a cell aggregation whereby the state of its change toward becoming multi-layered is determined. The image processing device 100 calculates the spatial luminance distribution and temporal luminance change of a small region within a cell aggregation for the entire region of the cell aggregation (in a designated analysis range in a case in which an analysis range is designated using a mouse or the like), and determines the state of change of the cell aggregation toward becoming multi-layered on the basis of the calculated spatial distribution and time lapse change of the pixel values.

Figure 1:
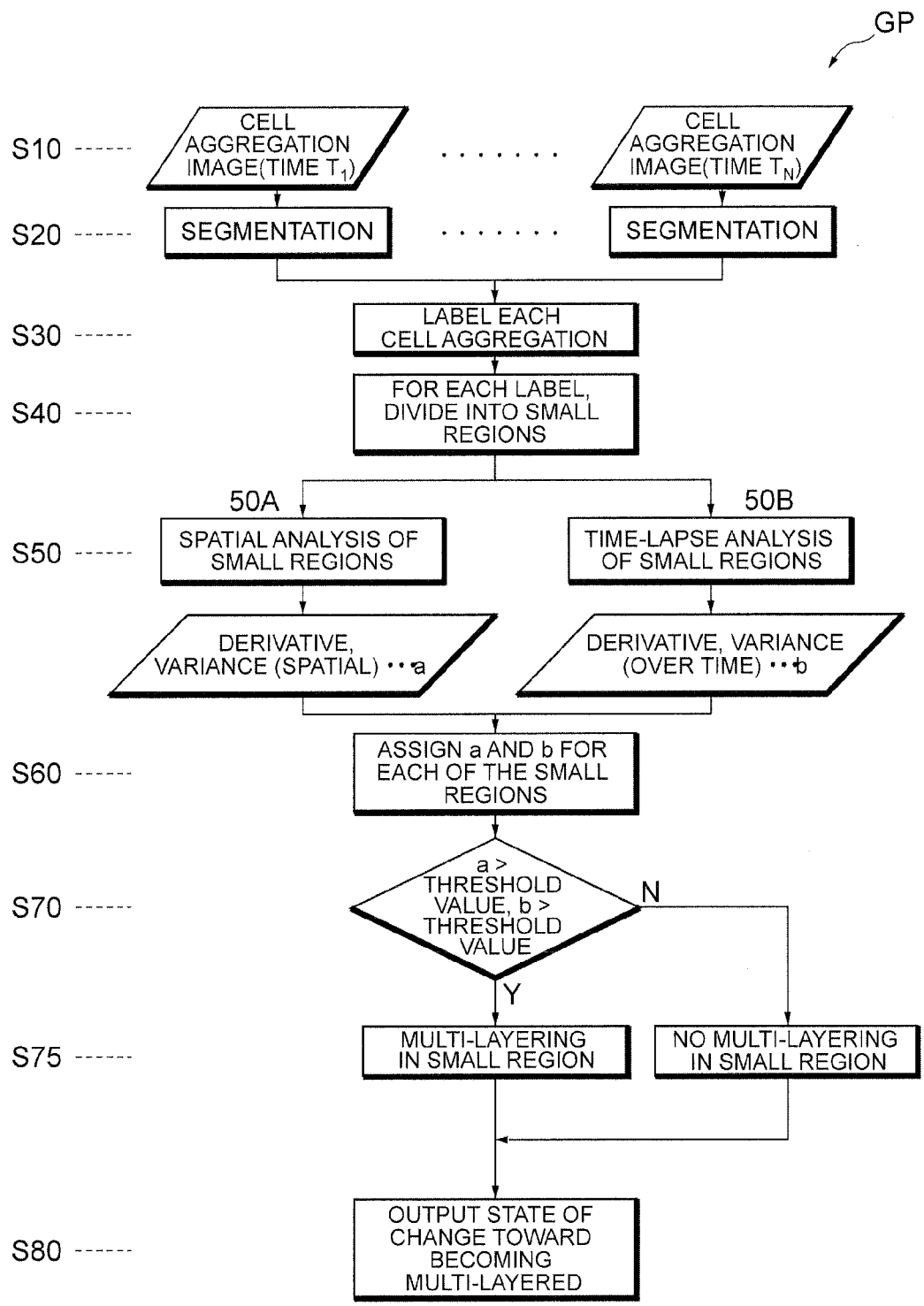
FIG. 1 is a flow chart illustrating an overview of the configuration of an image processing program
Figure 4:
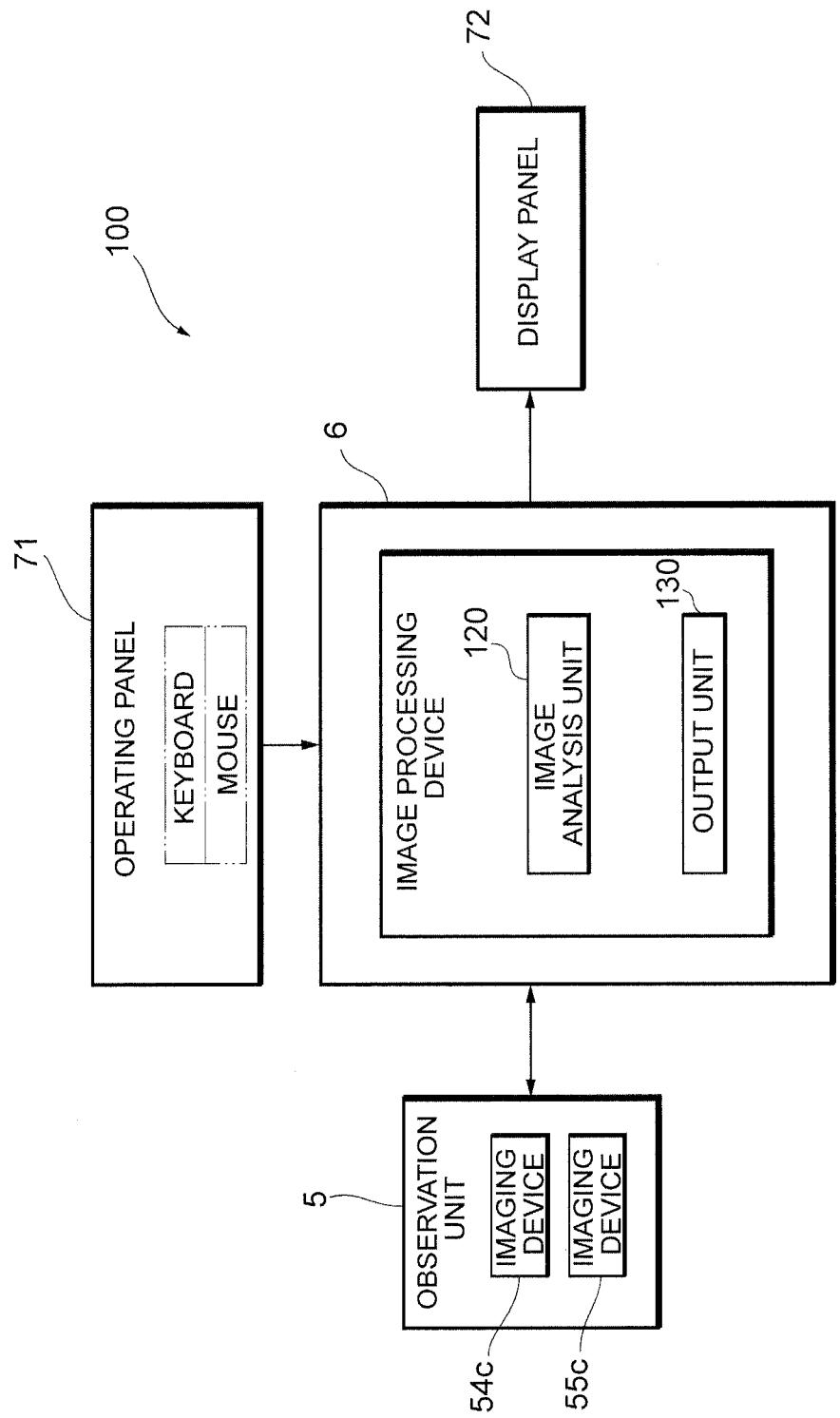
FIG. 4 is a block diagram illustrating an overview of an example of a configuration of an image processing device.

FIG. 4 is a block diagram illustrating the image processing device 100, and FIG. 1 is a flow chart illustrating the image processing program GP for running processing to determine multi-layering.

The image processing device 100 is configured to be provided with an image analysis unit 120 for obtaining and analyzing the time lapse images taken by the imaging devices (55c, 54c) and with an output unit 130 for outputting the analytical results analyzed by the image analysis unit 120, and is configured such that the analytical results from the image analysis unit 120 are outputted from the output unit 130 and displayed on the display panel 72 or the like; for example, information on the position and/or size of a site where multi-layering is decided to have occurred (surface area, volume, the ratio thereof, or the like), a determination between a cell aggregation that includes and a cell aggregation that does not include a multi-layered site, or the like.

The image processing program GP, which is set and stored in the ROM 62, is read into the CPU 61, and processing based on the image processing program GP is executed sequentially by the CPU 61, whereby the image processing device 100 is configured. In other words, the image processing program GP is software serving to cause the CPU 61 (a computer), which is a hardware resource, to function as the image processing device 100.

The image analysis unit 120 runs the following image processing on the basis of the image processing program GP for time lapse images of a cell aggregation, which are taken by an imaging device (for the purpose of description, refers here to the imaging device 55c of the micro system) and recorded in the RAM 63. The images taken by the imaging device 55c may also be processed sequentially in real time.

Figure 6:
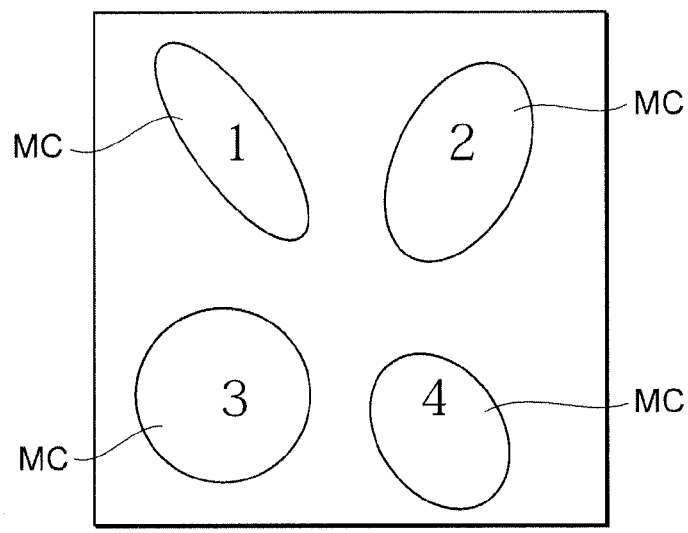
FIG. 6 is a schematic illustrating an example of the status of a cell aggregation that has been segmented and labeled.

The image analysis unit 120 obtains a sequence of time lapse images of cell aggregations stored in the RAM 63 (step S10) and segments the cell aggregations by the level set method and variance filtering for each of the images at times $t_1 \ldots t_n$ (step S20). Next, as illustrated in FIG. 6, the segmented cell aggregations MC are labeled (step S30), and associations are made for the cell aggregations between the images. For example, the cell aggregations MC given the labels 1, 2, 3 . . . in each of the images are associated, where a label that overlaps between images represents the same cell aggregation.

Next, cell aggregations with the same label are aligned in order to reduce the effects of cases in which the cell aggregations MC move. The position of the center of gravity of the cell aggregation, the vertex positions of the rectangular contour thereof, or the like is used as a standard for alignment; alignment can be done by calculating the amount of movement between the images, and the angle of rotation of the cell aggregations can be accounted for so as to maximize the correlation of the moment of the shape (minimize the difference). The alignment may be done at the position and angle at which the difference between a first image of time $t_1$ and a second image of time $t_2$ reaches a minimum (the correlation value reaches a maximum).

Figure 7:
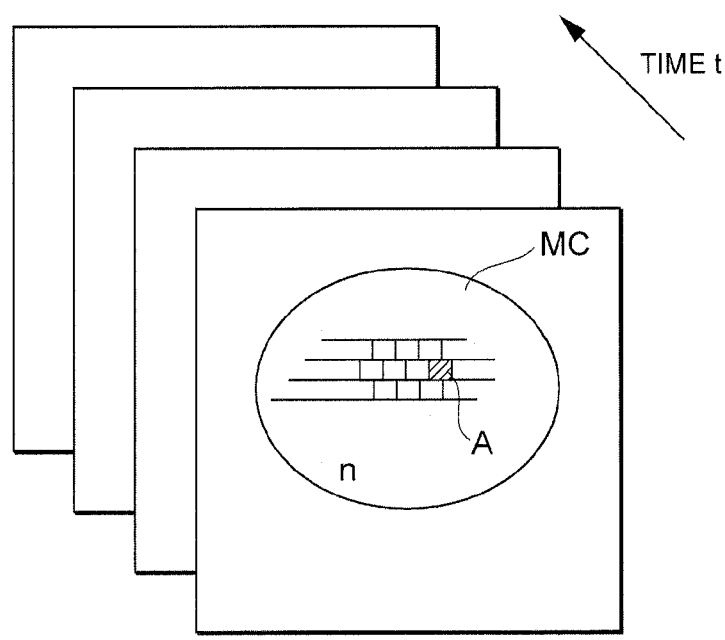
FIG. 7 is a schematic illustrating an example of obtaining the time lapse of a cell aggregation with the label n.

The time lapse images of a cell aggregation associated and aligned in this manner with the same label (FIG. 7 illustrates the time lapse images of a cell aggregation with the label n) are divided in step S40 into a plurality of "small regions" centered on the pixels forming the images. A small region A is set as a local region sufficiently smaller than the size of the cell aggregation MC, and is set to, for example, approximately 10×10 to 30×30 pixels (which is the size of approximately 2 to 5 cells).

Then, in step S50, the images are analyzed. The image analysis is constituted of a small region spatial analysis 50A and a small region time lapse analysis 50B.

(50A: Small-Region Spatial Analysis)

In the small region spatial analysis, the spatial change (disparity) of pixel values is calculated for each of the small regions in each of the time lapse images from the luminance distribution of the small region A. Examples of criteria for evaluating the spatial change of pixel values include, for the small region A, the variance of pixel values and/or derivative sum of pixel values relative to a spatial direction, the characteristics of the spatial change of pixel values being expressed quantitatively by this value (score) a. A small region in which the score a is high is a region in which the pixel values have major spatial change, and corresponds to a site in a cell aggregation that has become multi-layered or to a portion of the boundary between the interior and exterior of the cell aggregation.

(50B: Small-Region Time-Lapse Analysis)

In the small region time lapse analysis, the temporal change (disparity) of pixel values of the small region A in the time lapse images is calculated. Examples of criteria for evaluating the temporal change of the pixel values include the variance and/or derivative of pixel values of the small region A between time lapse images; the characteristics of the temporal change of pixel values can be expressed quantitatively by this value (score) b. A small region in which the score b is high is a region in which the pixel values have major temporal change, and corresponds to a portion in a cell aggregation that has become multi-layered.

In the "small-region pixel value" of a case in which the score b is calculated, the score a (the variance or derivative sum of pixel values) calculated in 50A can be employed; by such a configuration, the processing load on the CPU 61 can be reduced and the computational processing thereof can be accelerated. Further, the pixel value of at least any one pixel of the plurality of pixels forming the small region A or an appropriate mean pixel value of a plurality of pixels can also be used for the pixel value of the small region.

In step S60, the score a of the spatial change of pixel values and the score b obtained in the manner described above are assigned to respective small regions of the cell aggregation MC, and a map to which the scores a and b are attached is formed for the entire region of the cell aggregation.

Then, in step S70, a decision is made for each small region of the cell aggregation MC as to whether or not the score a is at or above a predetermined threshold value, and as to whether or not the score b is at or above a predetermined threshold value. In step S75, a region in which both the scores a and b are at or above the threshold values is classified as a region that has become multi-layered, and a region in which this is not true is classified as the remaining region (see also FIG. 5). For the score a of the small region when the decision is made in step S70, it is possible to use the sum $\Sigma(a_1 \ldots a_n)$, the mean, or other parameter of the scores $a_1$ to $a_n$ in the small region at each of the times in the time lapse images. Each of the aforementioned threshold values is a value that is appropriately set in accordance with the type of cell that is to be observed, the observation conditions, the analysis conditions, or other parameters. In the decision that a region has become multi-layered, a region in which the scores a×b are at or above a predetermined threshold value may be regarded as a region that has become multi-layered.

In step S80, the state of the cell aggregation toward becoming multi-layered is outputted from the output unit 130 on the basis of the results from the classification of step S75 and then displayed on the display panel 72 or other device. As illustrated in, for example, the schematic view of FIG. 8, the state of change of the cell aggregation toward becoming multi-layered is displayed such that within the image of the cell aggregation MC of label n, a region for which it has been decided that multi-layering has occurred can be recognized by hatching, color coding, or the like. Information on the size of the cell aggregation of label n that accounts for the multi-layered region (the surface area, the volume, the ratio thereof, or other parameter) is also displayed by numerical data.

Figure 8:
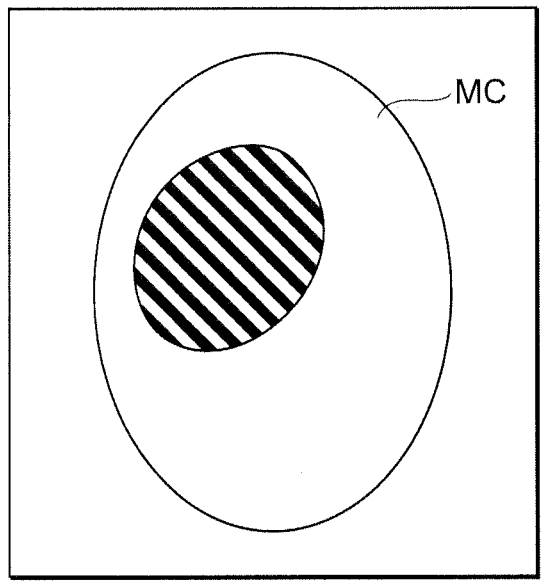
FIG. 8 is a schematic illustrating an example of the output mode of a multi-layered site (position, size, range) that has been determined by image analysis.

FIG. 8 illustrates an example of a configuration in which a specific cell aggregation (of label n) selected using a mouse or the like is enlarged and displayed; however, in a case where the image includes a plurality of cell aggregations MC, such as in FIG. 6, the display screen is replaced by the entire image, whereby it is possible to identify a cell aggregation that includes a site where multi-layering has occurred and a cell aggregation that does not contain one.

Examples of specific modes of such an identification display in the entire image include display modes in which, for example, the display for each cell aggregation in the image is similar to that of FIG. 8, or, alternatively, in which, for classification, a cell aggregation having a site where multi-layering has occurred is displayed as being yellow and a cell aggregation without any sites where multi-layering has occurred is displayed as blue, or in which the identification is displayed in accordance with the ratio of the surface area of each cell aggregation that accounts for a site where multi-layering has occurred, where a cell aggregation with a higher surface area ratio is redder, becoming yellow, green, or blue as the surface area ratio decreases. The configuration may be such that the analysis results are outputted to and recorded using a printer or the RAM 63, a magnetic recording medium, or the like; or outputted outside the system via the communication unit 65.

The observer is thereby able to make a quantitative, visual decision of the state of change of a cell aggregation toward becoming multi-layered, as included in the image. The state of the cell aggregation toward becoming multi-layered is thus determined in the image processing device 100 from the spatial distribution of luminance and the temporal change of a small region of the cell aggregation. Therefore, according to the technique for determining the state of a cell aggregation using the image processing device 100, there can be provided means by which the state of change of a cell aggregation toward becoming multi-layered can be determined from time lapse images taken by an imaging device (55c, 54c) without the cells being damaged due to the administration of a reagent.

The embodiment described above provides an example of a configuration of the cell culture observation system BS in which time lapse images (image data) that have been taken with an imaging device and stored in the RAM 63 are read out and the state of change toward becoming multi-layered is analyzed. However, the configuration may be such that images taken by an imaging device are sequentially analyzed in real time, or the configuration may be such that time lapse images that have been taken in another observation system and recorded in a magnetic storage medium or the like are read out and the state of change toward becoming multi-layered is analyzed. The configuration may also be such that an operator uses a mouse or the like to set a predetermined range of the cell aggregations included in the time lapse images (a specific cell aggregation, or a specific site in a cell aggregation) as an analysis range, and the image processing device executes an analysis of the state of change toward becoming multi-layered for the analysis range that has been set.

Figure 9:
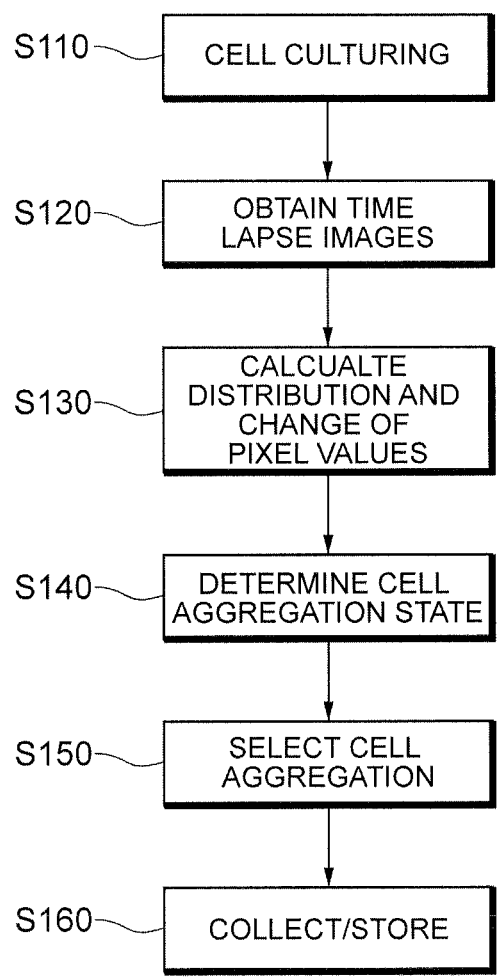
FIG. 9 is a flow chart illustrating a method for producing a cell aggregation.

The following is a description of the method for producing a cell aggregation according to an embodiment of the present invention, with reference to FIG. 9. Specifically, the method for producing a cell aggregation comprises a cell culture step for culturing cells (S110) and determination steps for observing, using the above-described image processing device, the cell cultured in the cell culture step and determining the state of change of a cell aggregation toward becoming multi-layered in the cells, which vary by cell culture (S120-S140).

More specifically, the method for producing a cell aggregation is configured to comprise a cell culture step for culturing cells (S110), an obtainment step for taking an image, by an imaging device, of the cell cultured in the cell culture step and acquiring time lapse images of a cell aggregation in the cells, which vary by cell culture (S120); a calculation step for calculating the spatial distribution of pixel values and the temporal change in pixel values of a small region in a cell aggregation that is in the time lapse images obtained in the obtainment step (S130); a determination step for determining the state of change of a cell aggregation toward becoming multi-layered on the basis of the spatial distribution and time lapse change of the pixel values calculated in the calculation step (S140); a selection step for selecting a cell aggregation on the basis of predetermined criteria (S150); and a collection and storage step in which the selected cell aggregation is collected and stored (S160). The cells that are cultured may be human-derived cells; cells derived from cows, horses, pigs, mice, or other animals; or plant-derived cells. The cell aggregation may be stored using cryogenic storage.

EXPLANATION OF NUMERALS AND CHARACTERS

A: Small region
BS: Cell culture observation system
GP: Image processing program
MC: Cell aggregation
5: Observation unit
6: Control unit
54: Macro observation system
54c: Imaging device
55: Microscope observation system
55c: Imaging device
61: CPU (computer)
62: ROM
63: RAM
100: Image processing device
120: Image analysis unit
130: Output unit

The invention claimed is:

1. A technique for determining the state of a cell aggregation, comprising:
   obtaining time lapse images of a cell aggregation taken by an imaging device;
   calculating a spatial distribution of pixel values and a temporal change of pixel values of a region in the cell aggregation in the obtained images; and
   determining a state of change of the cell aggregation toward becoming multi-layered on the basis of the calculated spatial distribution, the calculated time lapse change of the pixel values and at least one threshold value.

2. The technique for determining the state of a cell aggregation according to claim 1, wherein:
   the at least one threshold value includes first and second threshold values: and
   in the determination of the state of change toward becoming multi-layered, a cell aggregation is determined to have become multi-layered when the spatial change of pixel values in the region is at or above the first threshold value and the temporal change of pixel values is at or above the second threshold value.

3. The technique for determining the state of a cell aggregation according to claim 2, wherein the spatial change of pixel values is a variance of pixel values or a derivative sum of pixel values in the region.

4. The technique for determining the state of a cell aggregation according to claim 2, wherein the temporal change of pixel values is a variance or derivative of pixel values of corresponding regions in the time lapse images.

5. An image processing program encoded on a nontransitory computer readable medium under the control of a computer, to cause the computer to execute obtaining time lapse images of a cell aggregation taken by an imaging device;
   calculating a spatial distribution in pixel values and a temporal change in pixel values of a region in the cell aggregation in the obtained images;
   determining a state of change of the cell aggregation toward becoming multi-layered on the basis of the calculated spatial distribution, the calculated temporal change in pixel value and at least one threshold value; and
   outputting results of the determining.

6. The image processing program according to claim 5, wherein the at least one threshold value includes first and second threshold values, and wherein the determining a state of change of a cell aggregation toward becoming multi-layered is configured such that a cell aggregation is determined to have become multi-layered when the spatial change of pixel values in the region is at or above the first threshold value and the temporal change of pixel values is at or above the second threshold value.

7. The image processing program according to claim 6, wherein the spatial change of pixel values is a variance of pixel values or a derivative sum of pixel values in the region.

8. The image processing program according to claim 6, wherein the temporal change of pixel values is a variance or derivative of pixel values of corresponding small regions in the time lapse images.

9. The image processing program according to claim 5, wherein the outputting the determination results is configured such that information is outputted in regard to the position in the cell aggregation of a site where multi-layering is decided to have occurred in the determining the state of change of the cell aggregation toward becoming multi-layered.

10. The image processing program according to claim 5, wherein the outputting the determination results is configured such that information is outputted in regard to the size of the cell aggregation that accounts for a site where multi-layering is decided to have occurred in the determining the state of change of the cell aggregation toward becoming multi-layered.

11. The image processing program according to claim 5, wherein when each of the images of the time lapse includes a plurality of cell aggregations,
   the determining the state of change of the cell aggregations toward becoming multi-layered determines the states of change of each of the cell aggregations toward becoming multi-layered and distinguishes between cell aggregations having multi-layered sites and cell aggregations having no multi-layered sites; and
   the outputting the determination results is configured such that the determination results that have been distinguished are outputted.

12. An image processing device comprising:
   an image analysis unit to obtain time lapse images of a cell aggregation taken by an imaging device and analyzing the images, and
   an output unit to output the analysis results from the image analysis unit,
   the image analysis unit calculating the spatial distribution of pixel values and the temporal change of pixel values of a region in a cell aggregation within the obtained images, and determining the state of change of the cell aggregation toward becoming multi-layered, on the basis of the calculated spatial distribution and time lapse changes of the pixel values; and
   the output unit outputting the state of change of the cell aggregation toward becoming multi-layered as determined by the image analysis unit.

13. The image processing device according to claim 12, wherein the image analysis unit is configured such that a cell aggregation is determined to have become multi-layered when the spatial change of pixel values in the region is at or above a first threshold value and the temporal change of pixel values is at or above a second threshold value.

14. The image processing device according to claim 13, wherein the spatial change of pixel values is a variance of pixel values or a derivative sum of pixel values in the region.

15. The image processing device according to claim 13, wherein the temporal change of pixel values is a variance or derivative of pixel values of corresponding regions in the time lapse images.

16. The image processing device according to claim 12, wherein the image analysis unit calculates the position in the cell aggregation of a site where multi-layering is decided to have occurred; and the output unit outputs the information position of the multi-layering as calculated by the image analysis unit.

17. The image processing device according to claim 12, wherein the image analysis unit calculates the size of the cell aggregation that accounts for the site where multi-layering is decided to have occurred; and the output unit outputs the information of the size of multi-layering as calculated by the image analysis unit.

18. The image processing device according to claim 12, wherein when each of the images of the time lapse includes a plurality of cell aggregations, the image analysis unit determines the states of change of each of the cell aggregations toward becoming multi-layered and distinguishes between cell aggregations having multi-layered sites and cell aggregations having no multi-layered sites; and the output unit outputs the determination results that have been distinguished.

19. A method, comprising:
culturing cells;
observing, using the image processing device according to claim 12, the cells cultured in the culturing, and
determining the state of change of a cell aggregation toward becoming multi-layered in the cells, which vary by cell culture.

20. A method, comprising:
culturing cells;
taking an image, by an imaging device, of the cells cultured in the culturing and obtaining time lapse images of a cell aggregation in the cells, which vary by cell culture;
calculating the spatial distribution of pixel values and the temporal change in pixel values of a region in a cell aggregation that is in the time lapse images obtained in the taking; and
determining the state of change of a cell aggregation toward becoming multi-layered on the basis of at least one threshold value and the spatial distribution and time lapse change of the pixel values calculated in the calculating.

* * * * *

UNITED STATES PATENT AND TRADEMARK OFFICE
CERTIFICATE OF CORRECTION

PATENT NO. : 8,588,504 B2
APPLICATION NO. : 13/315794
DATED : November 19, 2013
INVENTOR(S) : Kazuhiro Yano et al.

Page 1 of 1

It is certified that error appears in the above-identified patent and that said Letters Patent is hereby corrected as shown below:

Title Page, Item (54) and in the Specification, In Column 1, Line 2, (Title), Delete "AGGREGATION" and insert -- AGGREGATION, --, therefor.

In the Claims
In Column 11, Line 65, In Claim 5, Delete "pixel value" and insert -- pixel values --, therefor.

Signed and Sealed this
Twenty-fifth Day of March, 2014

Michelle K. Lee
*Deputy Director of the United States Patent and Trademark Office*